United States Patent
Zhou et al.

(10) Patent No.: US 12,304,937 B2
(45) Date of Patent: May 20, 2025

(54) LEPTIN IMMUNOGENS, HYBRIDOMA CELLS, MONOCLONAL ANTIBODIES, POLYCLONAL ANTIBODIES AND USE THEREOF

(71) Applicant: SHENZHEN YHLO BIOTECH CO., LTD, Shenzhen (CN)

(72) Inventors: Mi Zhou, Shenzhen (CN); Yujian Lin, Shenzhen (CN); Chungen Qian, Shenzhen (CN); Kunhui Hu, Shenzhen (CN)

(73) Assignee: SHENZHEN YHLO BIOTECH CO., LTD, Shenzhen (CN)

( * ) Notice: Subject to any disclaimer, the term of this patent is extended or adjusted under 35 U.S.C. 154(b) by 551 days.

(21) Appl. No.: 17/424,484

(22) PCT Filed: Dec. 24, 2019

(86) PCT No.: PCT/CN2019/127876
§ 371 (c)(1),
(2) Date: Jul. 20, 2021

(87) PCT Pub. No.: WO2020/253187
PCT Pub. Date: Dec. 24, 2020

(65) Prior Publication Data
US 2022/0144912 A1 May 12, 2022

(30) Foreign Application Priority Data
Jun. 21, 2019 (CN) .......................... 201910543495.5

(51) Int. Cl.
*C07K 14/575* (2006.01)
*C07K 16/26* (2006.01)
*G01N 33/74* (2006.01)

(52) U.S. Cl.
CPC .......... *C07K 14/5759* (2013.01); *C07K 16/26* (2013.01); *G01N 33/74* (2013.01)

(58) Field of Classification Search
None
See application file for complete search history.

(56) References Cited

U.S. PATENT DOCUMENTS

| | | | |
|---|---|---|---|
| 6,124,439 A | 9/2000 | Friedman et al. | |
| 6,277,592 B1 | 8/2001 | Bidwell et al. | |

FOREIGN PATENT DOCUMENTS

| | | | |
|---|---|---|---|
| CN | 1221426 A | 6/1999 | |
| CN | 1246154 A | 3/2000 | |
| CN | 103957926 A | 7/2014 | |
| CN | 106405117 A | 2/2017 | |
| CN | 108051600 A | 5/2018 | |
| CN | 110183530 A | 8/2019 | |
| WO | 9623815 A1 | 8/1996 | |
| WO | 0011173 A1 | 3/2000 | |
| WO | 2005049655 A1 | 6/2005 | |
| WO | 2005094259 A2 | 10/2005 | |

OTHER PUBLICATIONS

European Patent Office, the Extended European Search Report Issued in Application No. 19933626.4, May 16, 2023, Germany, 8 pages.
Jafar Mahmoudian et al.,"A Monoclonal Antibody Against Leptin", Hybridoma, vol. 31, No. 5, Oct. 1, 2012, pp. 372-377.
"Human Leptin Elisa Kit 96-Well Plate (Cat. # EZHL-80SK)", Jul. 19, 2005, total 23 pages.
Li Ming et al.,"A highly sensitive enzyme-linked immunosorbent assay for measurement of leptin secretion in human adipocytes", Department of Endocrinology, Peking Union Medical College Hospital, Peking Union Medical College Hospital, Beijing 100730,China, pp. 3293-3297, Natl Med J China, Dec. 16, 2018, vol. 88, No. 46.
Keiichi Imagawa et al.,"Development of a sensitive ELISA for human leptin, using monoclonal antibodies", Clinical Chemistry, vol. 44, No. 10, pp. 2165-2171, Oct. 31, 1998.
Fengyin Li et al.,"Preparation of Human Leptin Monoclonal Antibody and Its Preliminary Application", Journal of Radioimmunology, vol. 13, No. 1, pp. 14-17, Feb. 29, 2000.
Patricia Grasso et al.,"Epitope mapping of secreted mouse leptin utilizing peripherally administered synthetic peptides", Journal of reproduction and development, vol. 85, No. 2-3, pp. 93-100, Dec. 23, 1999.
Toru Takahashi et al.,"Generation and Characterization of Anti-Leptin Antisera against Synthetic Peptides and Recombinant Protein", Journal of reproduction and development, vol. 50, No. 6, pp. 717-724, Dec. 31, 2004.
Vani Xavier De Oliveira Jr et al.,"In vitro evaluation of leptin fragments activity on the ob receptor", Journal of Peptide Science, vol. 14, No. 5, pp. 617-625, Nov. 16, 2007.
Mark P. Richards et al.,"Design and application of a polyclonal peptide antiserum for the universal detection of leptin protein", Journal of Biochemical and Biophysical methods, vol. 45, No. 2, total 12 pages, Oct. 2000.

*Primary Examiner* — Ilia I Ouspenski
(74) *Attorney, Agent, or Firm* — Kilpatrick Townsend & Stockton LLP

(57) ABSTRACT

Provided are a leptin immunogen, hybridoma cells, a monoclonal antibody, a polyclonal antibody and use thereof. The leptin immunogen includes a polypeptide having an amino acid sequence as shown in SEQ ID NO: 1. The anti-leptin monoclonal antibody prepared with the leptin immunogen has good specificity and high sensitivity.

7 Claims, No Drawings
Specification includes a Sequence Listing.

LEPTIN IMMUNOGENS, HYBRIDOMA CELLS, MONOCLONAL ANTIBODIES, POLYCLONAL ANTIBODIES AND USE THEREOF

FIELD

The present disclosure relates to a leptin immunogen, hybridoma cells, a monoclonal antibody, a polyclonal antibody, and use thereof.

BACKGROUND

Leptin is a protein that derived from a single-chain protein having 167 amino acid residues, which is encoded by human ob gene, and after which is secreted from adipocytes into the plasma, 21 amino acid residues at its amino-terminus are removed under the action of signal peptidase. Thus, leptin present in plasma is 146 amino acid residues in full length and has a molecular weight of about 16 kDa. Leptin has good hydrophilicity. About 80% of leptin in plasma is bound to plasma proteins, and only a small amount of leptin in plasma exists in free form. Leptin exerts biological effects through the specific receptors that are widely found in different tissues and organs (such as the central nervous system, fat, heart, liver, lung, kidney, and pancreas, etc.) and the corresponding signal transduction systems, and participates in the regulation of metabolism of sugar, fat and energy.

Studies have found that leptin levels in humans will change under a variety of physiological and pathological conditions, which has very significant clinical guidance value for the occurrence, development, prognosis, and medication efficacy test of many energy metabolism-related diseases. For example, the leptin level in the body has a certain positive significance for the prevention and treatment of obesity since the serum leptin concentration in obese patients is higher than that in non-obese patients; the serum leptin level in patients with malignant tumors is significantly higher than that in a normal control, and will be reduced accordingly after treatment, indicating that leptin may be used as an indicator for evaluating the condition of patients with malignant tumors and monitoring the efficacy before and after medication; and leptin has certain clinical value in determining the condition of pregnancy-induced hypertension, since the serum leptin level will be gradually increased with the progress of pregnancy in normal pregnancy, and will also be on the rise when hypertension of pregnancy occurs. In a word, leptin is related to a variety of acute and chronic diseases, and can be better applied in clinical practice as people deepen their knowledge.

At present, methods for detecting leptin mainly depend on the specific binding ability of leptin antibodies to leptin in the test sample. Thus, the specificity and sensitivity of anti-leptin antibodies for leptin are very important for the measurement of leptin content.

However, currently, there are fewer anti-leptin antibodies with better specificity and higher sensitivity on the market, which cannot meet the market demand.

SUMMARY

Accordingly, it is necessary to provide a leptin immunogen. An anti-leptin monoclonal antibody with better specificity and higher sensitivity can be prepared using the leptin immunogen.

In addition, hybridoma cells secreting an anti-leptin monoclonal antibody with better specificity and higher sensitivity, a monoclonal antibody, a preparation method and use thereof are provided.

A leptin immunogen includes a polypeptide having an amino acid sequence as set forth in SEQ ID NO. 1.

The leptin immunogen as above includes a polypeptide having an amino acid sequence as set forth in SEQ ID NO. 1. An anti-leptin monoclonal antibody prepared using the leptin immunogen can specifically recognize amino acid residues at positions 41 to 60 of leptin at the amino-terminus, and has a higher affinity to leptin and higher sensitivity.

In an embodiment, the leptin immunogen further includes a carrier protein conjugated to the polypeptide.

A method for preparing hybridoma cells secreting an anti-leptin monoclonal antibody includes:
  immunizing an animal with an immunogen to obtain spleen cells from the immunized animal, and the immunogen is the leptin immunogen as above;
  fusing the spleen cells to myeloma cells and then screening to obtain positive fused cells; and
  subcloning the positive fused cells to obtain the hybridoma cells secreting the anti-leptin monoclonal antibody.
  hybridoma cells secreting an anti-leptin monoclonal antibody is prepared by the above-mentioned method for preparing hybridoma cells secreting an anti-leptin monoclonal antibody.

An anti-leptin monoclonal antibody is secreted from hybridoma cells secreting the anti-leptin monoclonal antibody as above.

A leptin immunogen includes a polypeptide having an amino acid sequence as set forth in SEQ ID NO. 2.

In an embodiment, the leptin immunogen further includes a carrier protein conjugated to the polypeptide.

A method for preparing an anti-leptin polyclonal antibody includes:
  immunizing an animal with the leptin immunogen as above to obtain the anti-leptin polyclonal antibody.

An anti-leptin polyclonal antibody is prepared by the method for preparing the anti-leptin polyclonal antibody.

Use of at least one of the anti-leptin monoclonal antibody as above and the anti-leptin polyclonal antibody as above in preparation of a leptin detection reagent, a leptin detection test paper or a leptin detection kit is provided.

A leptin detection reagent includes at least one of the anti-leptin monoclonal antibody as above and the anti-leptin polyclonal antibody as above.

A leptin detection kit includes the leptin detection reagent as above.

DETAILED DESCRIPTION OF THE EMBODIMENTS

In order to understand the present disclosure, the present disclosure will be described more fully hereinafter. The present disclosure may be embodied in many different forms and should not be construed as limited to the embodiments set forth herein. Rather, these embodiments are provided so that this disclosure will be thorough and complete.

All scientific terms used herein have the same meaning as commonly understood in the art to which this disclosure belongs unless otherwise defined. The terms used in the description herein are only for the purpose of describing specific embodiments, and are not intended to limit the present disclosure.

An embodiment of the present disclosure provides a leptin immunogen. An anti-leptin monoclonal antibody secreted by the hybridoma cells prepared using the leptin immunogen can specifically recognize the antigen epitope at the amino-terminus of leptin, has a strong affinity to leptin and high sensitivity, and is applicable for the preparation of a leptin detection reagent, a leptin detection test paper, and a leptin detection kit.

In one embodiment, the leptin immunogen includes a polypeptide having an amino acid sequence as set forth in SEQ ID NO. 1. The amino acid sequence as set forth in SEQ ID NO. 1 is RINDISHTQSVSSKQKVTGL. The leptin immunogen as above is designed to aim at the amino-terminus of leptin. The amino acid sequence as set forth in SEQ ID NO. 1 is identical to the amino acids at positions 41 to 60 of the human leptin full-length amino acid sequence, and is far away from the carboxyl-terminus of leptin. The antibody obtained from immunizing an animal with the above-mentioned leptin immunogen comprising the polypeptide having the amino acid sequence as set forth in SEQ ID NO. 1 can specifically recognize the amino-terminus of leptin and has a strong affinity, avoiding interference with recognition and binding of other antibodies to the carboxyl-terminus of leptin.

In an embodiment, the leptin immunogen further includes a carrier protein conjugated to the polypeptide having the amino acid sequence as set forth in SEQ ID NO. 1. The carrier protein conjugated to the polypeptide as the immunogen is beneficial to stimulate helper T cells and further induces B cell immune response. In one embodiment, the carrier protein is one selected from hemocyanin (KLH), bovine serum albumin, chicken ovalbumin (OVA), rabbit serum albumin, and fibrinogen. In one embodiment, the carrier protein is one selected from hemocyanin and bovine serum albumin.

An embodiment of the present disclosure also provides a method for preparing hybridoma cells secreting an anti-leptin monoclonal antibody, comprising steps S110 to S150 as follows:

Step S110, immunizing an animal with an immunogen to obtain spleen cells from the immunized animal In one embodiment, the immunogen is the leptin immunogen in any of the above embodiments. Further, the immunogen includes a polypeptide having an amino acid sequence as set forth in SEQ ID NO. 1.

In an embodiment, the immunogen is mixed with Freund's complete adjuvant and fully emulsified, then injected into the mice followed by continuously booster immunization, and after measuring serum titer from the blood collected, the spleen of mice with a serum titer of $10^5$-$10^6$ is excised to obtain spleen cells from the immunized animal.

In one embodiment, the dose of the immunogen for the first immunization is in a range from 90 μg to 120 μg, and the dose of the immunogen for the last immunization is in a range from 0 μg to 60 μg, with an immunization interval in a range from 10 days to 21 days. Further, the dose of the immunogen for the first immunization is in a range from 100 μg to 110 μg, the dose of the immunogen for the last immunization is in a range from 40 μg to 50 μg, with an immunization interval in a range from 14 days to 21 days.

Step S130, fusing the spleen cells to myeloma cells and then screening to obtain positive fused cells In one embodiment, the spleen cells are fused to the mice myeloma cells and then selective culturing and screening to obtain the positive fused cells.

In one embodiment, the positive fused cells secreting anti-leptin antibodies are screened out using the amino acid sequence as set forth in SEQ ID NO. 1.

Step S150, subcloning the positive fused cells to obtain the hybridoma cells secreting the anti-leptin monoclonal antibody In one embodiment, the subcloning is performed by limiting dilution method to obtain the hybridoma cells capable of stably secreting the anti-leptin monoclonal antibody.

In the method for preparing the hybridoma cells secreting the anti-leptin monoclonal antibody, the animal is immunized with the leptin immunogen in any of the above embodiments as the immunogen to obtain the hybridoma cells that can stably secrete the anti-leptin monoclonal antibody. Meanwhile, this monoclonal antibody can specifically recognize the epitope at the amino-terminus of leptin, and has high affinity and specificity to leptin.

An embodiment of the present disclosure also provides hybridoma cells secreting an anti-leptin monoclonal antibody. The hybridoma cells are prepared by the above-mentioned method for preparing the hybridoma cells secreting an anti-leptin monoclonal antibody. The anti-leptin monoclonal antibody secreted by the hybridoma cells is designated as LEP-Ab-01. The LEP-Ab-01 can specifically recognize the surface antigen of leptin at the amino-terminus and has high affinity and high specificity.

The present disclosure also provides an anti-leptin monoclonal antibody that is secreted by hybridoma cells prepared by the above-mentioned method for preparing the hybridoma cells secreting an anti-leptin monoclonal antibody. Further, the monoclonal antibody is LEP-Ab-01. LEP-Ab-01 is a monoclonal antibody with the highest titer that is secreted by hybridoma cells prepared by the above-mentioned method for preparing the hybridoma cells secreting an anti-leptin monoclonal antibody.

The anti-leptin monoclonal antibody as described above can specifically recognize the amino terminus of human leptin, and has high affinity and specificity to human leptin. In addition, the recognized site is far away from the carboxyl-terminus of leptin, avoiding interference with recognition and binding of other antibodies to the carboxyl-terminus of leptin. The anti-leptin monoclonal antibody is widely applicable in the field of leptin detection, such as in the preparation of a detection reagent, a detection test paper, a detection kit, etc. for detecting leptin, and thus has significant advantages in terms of specificity, sensitivity and detection rate compared with conventional monoclonal antibodies.

In one embodiment, the anti-leptin monoclonal antibody as above can be used as a capture antibody. The capture antibody is used to capture the antigen in a sample to be tested. The anti-leptin monoclonal antibody as above can be used as a detection antibody. The detection antibody is used to bind to the captured antigen for detection.

An embodiment of the present disclosure also provides another leptin immunogen. A polyclonal antibody prepared using the leptin immunogen can specifically recognize an epitope of leptin near its carboxyl end, has better specificity and higher sensitivity and is applicable for the preparation of a leptin detection reagent, a leptin detection test paper, and a leptin detection kit.

In one embodiment, the leptin immunogen includes a polypeptide having an amino acid sequence as set forth in SEQ ID NO. 2. The amino acid sequence as set forth in SEQ ID NO. 2 is SCHLPWASGLETLDSLGGVLEASGY.

Studies have found that the amino acid residues at positions 106 to 120, 116 to 130, and 126 to 140 at the carboxyl terminus of leptin have significant physiological functions and have significant activities. The above-mentioned leptin immunogen comprising the amino acid sequence as set forth in SEQ ID NO. 2 is designed to aim at the carboxyl-terminus of leptin. The amino acid sequence as set forth in SEQ ID NO. 2 is identical to the amino acids at positions 116 to 140 of the human leptin full-length amino acid sequence, and is far away from the amino-terminus of leptin. The antibody obtained from immunizing an animal with the above-mentioned leptin immunogen comprising the polypeptide having the amino acid sequence as set forth in SEQ ID NO. 2 can specifically recognize the carboxyl-terminus of leptin and has a strong affinity, avoiding interference with recognition and binding of other antibodies to the amino-terminus of leptin.

In an embodiment, the leptin immunogen further includes a carrier protein conjugated to the polypeptide having the amino acid sequence as set forth in SEQ ID NO. 2. The carrier protein conjugated to the polypeptide as the immunogen is beneficial to stimulate helper T cells and further induces B cell immune response. In one embodiment, the carrier protein is one selected from hemocyanin (KLH), bovine serum albumin, chicken ovalbumin (OVA), rabbit serum albumin, and fibrinogen. In one embodiment, the carrier protein is one selected from hemocyanin and bovine serum albumin.

An embodiment of the present disclosure also provides a method for preparing an anti-leptin polyclonal antibody, comprising steps S210 to S230 as follows:

Step S210, immunizing an animal with an immunogen to obtain the immunized animal.

In one embodiment, the immunogen includes a polypeptide having an amino acid sequence as set forth in SEQ ID NO. 2. Further, the immunogen also includes a carrier protein conjugated to the polypeptide having an amino acid sequence as set forth in SEQ ID NO. 2.

In an embodiment, rabbits are immunized with the immunogen multiple times to obtain the immunized rabbits. The dose of the immunogen for each immunization is in a range from 1 mg to 2 mg, with an immunization interval in a range from 10 days to 14 days. In one embodiment, the dose of the immunogen for each immunization is in a range from 1 mg to 1.5 mg. Naturally, the site that is to be immunized includes, but is not limited to, subcutis in the back, subcutis in the abdominal, subcutis in the armpit, and subcutis in the limb.

Step S230, extracting an anti-leptin polyclonal antibody from the immunized animal and purified the anti-leptin polyclonal antibody.

In one embodiment, the anti-leptin polyclonal antibody is isolated from the blood of the immunized animal and purified.

In the above-mentioned method for preparing the anti-leptin polyclonal antibody, the polypeptide having the amino acid sequence as set forth in SEQ ID NO. 2 is used as the immunogen to obtain the anti-leptin polyclonal antibody.

An embodiment of the present disclosure provides an anti-leptin polyclonal antibody that is prepared by the above-mentioned method for preparing the anti-leptin polyclonal antibody. Further, the polyclonal antibody is LEP-Ab-02.

The polyclonal antibody as described above can specifically recognize multiple epitopes of leptin, especially the epitope at the carboxyl-terminus of leptin, and has high specificity and affinity to natural leptin. The polyclonal antibody is applicable in the field of leptin detection, such as in the preparation of a leptin detection reagent, a leptin detection test paper, a leptin detection kit, etc.

Use of at least one of the anti-leptin monoclonal antibody as described above and the anti-leptin polyclonal antibody as described above in preparation of a leptin detection reagent, a leptin detection test paper or a leptin detection kit is provided.

An embodiment of the present disclosure provides a leptin detection reagent. The leptin detection reagent includes at least one of the anti-leptin monoclonal antibody as described above and the anti-leptin polyclonal antibody as described above. Further, the leptin detection reagent includes the anti-leptin monoclonal antibody as described above and the anti-leptin polyclonal antibody as described above. Even further, the leptin detection reagent includes LEP-Ab-01 and LEP-Ab-02.

In an embodiment, one of the above-mentioned anti-leptin monoclonal antibody and the above-mentioned anti-leptin polyclonal antibody coats together with magnetic particles, forming a capture antibody; while the other antibody of the above-mentioned anti-leptin monoclonal antibody and the above-mentioned anti-leptin polyclonal antibody is labeled, forming a detection antibody. Naturally, the labeling can be carried out by means commonly used in the art, such as fluorescein labeling, enzyme labeling, biotinylation labeling, and colloidal gold labeling. In an embodiment, acridine ester is selected as the label. The chemiluminescence immunoassay system using acridinium ester has a wide linear range from 0.5 ng/mL to 100 ng/mL. Additionally, acridinium ester is more cost-effective compared with enzyme-labeled materials.

The above-mentioned leptin detection reagent includes at least one of the anti-leptin monoclonal antibody as described above and the anti-leptin polyclonal antibody as described above. The above-mentioned leptin detection reagent also has good specificity and sensitivity in leptin detection.

An embodiment of the present disclosure further provides a leptin detection test paper. The leptin detection test paper includes a solid phase carrier and a capture antibody coating on the solid phase carrier. The capture antibody is one selected from the anti-leptin monoclonal antibody as described above and the anti-leptin polyclonal antibody as described above. In one embodiment, the solid phase carrier is a cellulose membrane.

Further, the leptin detection test paper further includes a detection antibody. The detection antibody is one selected from the above-mentioned anti-leptin monoclonal antibody which is labeled and the above-mentioned anti-leptin polyclonal antibody which is labeled. Even further, the capture antibody is the anti-leptin polyclonal antibody as described above, and the detection antibody is the anti-leptin monoclonal antibody as described above. Using the above-mentioned anti-leptin polyclonal antibody as the capture antibody can improve the detection sensitivity and specificity of the above-mentioned leptin detection test paper.

The above-mentioned leptin detection reagent comprising at least one of the anti-leptin monoclonal antibody as described above and the anti-leptin polyclonal antibody as described above also has good specificity and sensitivity in leptin detection.

An embodiment of the present disclosure further provides a leptin detection kit comprising the leptin detection test paper as described above and the leptin detection reagent as described above.

In an embodiment, the leptin detection kit further includes other detection reagents. Other test reagents, such as leptin standard samples, and buffers, can be provided as required in the detection.

The above-mentioned leptin detection kit includes the detection reagent or test paper containing at least one of the anti-leptin monoclonal antibody as described above and the anti-leptin polyclonal antibody as described above. Thus, the above-mentioned leptin detection kit also has good specificity and sensitivity in leptin detection. In addition, the leptin detection kit as above has good repeatability with stable results, compared with the plate-type magnetic microparticle chemiluminescence analysis kit using FITC as the labeling material. Compared with the latex-enhanced immunoturbidimetry kit using surface functional groups, the above-mentioned leptin detection kit has high sensitivity and specificity, and is not easily affected by blood lipid concentration.

EXAMPLES

A detailed description will be given below in conjunction with specific examples. The medicines and instruments used in the examples are conventional choices in the art unless otherwise specified. The experimental methods that do not specify specific conditions in the examples are implemented in accordance with conventional conditions, such as the conditions described in literature and books, or with the method recommended by the manufacturer.

Example 1

Preparation of Immunogen (1) a polypeptide having an amino acid sequence as set forth in SEQ ID NO. 1 and a polypeptide having an amino acid sequence as set forth in SEQ ID NO. 2 were synthesized by Sangon Biotech (Shanghai) Co., Ltd. The amino acid sequence as set forth in SEQ ID NO. 1 is RINDISHTQSVSSKQKVTGL, and the amino acid sequence as set forth in SEQ ID NO. 2 is SCHLPWAS-GLETLDSLGGVLEASGY.

(2) the polypeptide having the amino acid sequence as set forth in SEQ ID NO. 1 was conjugated to bovine serum albumin through the protein coupling technology, obtaining an immunogen for preparing an anti-leptin monoclonal antibody, which is designated immunogen 1.

(3) the polypeptide having the amino acid sequence as set forth in SEQ ID NO. 2 was conjugated to bovine serum albumin through protein coupling technology, obtaining an immunogen for preparing an anti-leptin polyclonal antibody, which is designated immunogen 2.

Example 2

Preparation of Anti-Leptin Monoclonal Antibody (1) the immunogen 1 prepared in Example 1 was mixed with an equal amount of Freund's complete adjuvant and fully emulsified before immunization of 3 BALB/c mice, with each immunized three times in total. For the first two immunizations, each mouse was immunized with immunogen 1 and Freund's complete adjuvant both in an injection amount of 100 μg at an immunization interval of 14 days. The third immunization was performed three days before the cell fusion: 50 μg of immunogen 1 was mixed with an equal amount of Freund's incomplete adjuvant and fully emulsified before immunization of mice. Then the immunized BALB/c mice were kept for three days, thus obtaining immunized mice.

(2) Cell fusion: spleen cells of the immunized mice were harvested, and fused with pre-cultured Sp2/0 myeloma cells (purchased from the American Type Culture Collection, ATCC) under PEG, thus obtaining fused cells.

(3) selective culturing and screening: the fused cells were cultured in HAT medium in 96-well cell culture plates, and after 7 days, the supernatant in the culture of fused cells was taken for ELISA detection. The coating antigen on the ELISA plate is the polypeptide having the amino acid sequence as set forth in SEQ ID NO. 1. Cells in the wells in which OD450 was higher than 1.5 were picked as positive fused cells.

(4) Cell cloning: the positive fused cells obtained in step (3) was subcloned three times by limiting dilution method, obtaining 7 hybridoma cell strains capable of stably secreting anti-leptin monoclonal antibodies, which were numbered 1 through 7, respectively. The monoclonal antibody secreted by hybridoma cell strain No. 1 was designated LEP-Ab-01.

(5) Ascites preparation: 8-week-old BALB/c mice were randomly divided into 5 groups 10 days after injection of paraffin, with each group of BALB/c mice corresponding to each hybridoma cell strain, respectively. Each of the hybridoma cell strains obtained in step (4) were cultured in large scale and injected into the abdomen of BALB/c mice in the corresponding group. After 7 days, ascites rich in antibodies were collected from the abdomen of BALB/c mice in each group.

(6) potency test on ascites:

The immunogen 1 was diluted 10-fold, $10^2$-fold, $10^3$-fold, $10^4$-fold, $10^5$-fold, $10^6$-fold respectively for detecting the ascites titer by indirect ELISA. Some of the test results were as shown in Table 1 below. In Table 1, "1 #" means the group corresponding to hybridoma cell strain No. 1, "2 #" means the group corresponding to hybridoma cell strain No. 2, and so on.

| Antigen | Antibody titer | | | | |
| --- | --- | --- | --- | --- | --- |
| dilution fold | 1# | 2# | 3# | 4# | 5# |
| 10 | 3.531 | 3.121 | 2.821 | 2.578 | 2.502 |
| $10^2$ | 3.232 | 2.635 | 2.135 | 2.015 | 1.635 |
| $10^3$ | 1.542 | 1.326 | 0.872 | 0.687 | 0.762 |
| $10^4$ | 0.562 | 0.438 | 0.358 | 0.276 | 0.368 |
| $10^5$ | 0.146 | 0.106 | 0.082 | 0.076 | 0.016 |
| $10^6$ | 0.035 | 0.011 | 0.022 | 0.022 | 0.032 |
| PBS | 0.011 | 0.012 | 0.008 | 0.011 | 0.012 |

(7) Purification and identification: the ascites of each group obtained in step (5) was purified by ammonium sulfate precipitation and Protein A affinity chromatography. In one embodiment, the ascites obtained in step (5) were each subjected to ammonium sulfate precipitation. In detail, ammonium sulfate powder was added to the ascites of each group under stirring, forming a saturated ammonium sulfate solution of each group within 5 min to 10 min. The stirring continued for 20 minutes, and then the solution was centrifuged at 10000×g for 10 minutes at 4° C. After discarding the supernatant, the pellet was suspended in 1×PBS of 2 times the volume of the pellet, then dialyzed in 1×PBS overnight to remove ammonium sulfate, to obtain a primary purified product.

Through a Protein A affinity chromatography column that had been equilibrated with 1×PBS, passed the primary purified product, followed by 1×PBS to remove the contaminant proteins that were not bound to the medium, and finally 0.1 M glycine for elution. The eluate was collected, obtaining a purified monoclonal antibody of each group. SDS-PAGE identification showed that the purified monoclonal antibody in each group had purity above 98%.

Example 3

Preparation of Anti-Leptin Polyclonal Antibody (1) Animal immunization: the immunogen 2 prepared in Example 1 was mixed with an equal amount of Freund's complete adjuvant and fully emulsified before injected into 2 New Zealand rabbits, with each rabbit in an amount of 1 mg of immunogen 2. Boost immunizations after an interval of 14 days: the immunogen 2 was mixed with an equal amount of Freund's incomplete adjuvant and fully emulsified before injected into the rabbits, with each rabbit in an amount of 1 mg of immunogen 2. Three boost immunizations were performed with the immunogen 2 and Freund's incomplete adjuvant both in 1 mg for each boost immunization. Before each boost immunization, 1 ml of ear arterial blood was collected for testing the antibody titer. Once the titer no longer increased, venous blood was collected for isolation and purification of anti-leptin polyclonal antibodies.

(2) Purification: the polyclonal antibodies obtained in step (1) was purified by ammonium sulfate precipitation and Protein A affinity chromatography. In one embodiment, the venous blood obtained in step (1) was centrifuged to obtain serum, which was then subjected to ammonium sulfate precipitation. In detail, ammonium sulfate powder was added to the ascites of each group under stirring, forming a saturated ammonium sulfate solution of each group within 5 min to 10 min. The stirring continued for 20 minutes, and the solution was centrifuged at 10000×g for 10 minutes at 4° C. After discarding the supernatant, the pellet was suspended in 1×PBS of 2 times the volume of the pellet, then dialyzed in 1×PBS overnight to remove ammonium sulfate, obtaining a primary purified product.

Through a Protein A affinity chromatography column that had been equilibrated with 1×PBS, passed the primary purified product, followed by 1×PBS to remove the contaminant proteins that were not bound to the medium, and finally 0.1 M glycine for elution. The eluate was collected, obtaining a purified polyclonal antibody, designated LEP-Ab-02.

Example 4

Pairing of Anti-Leptin Monoclonal Antibody with Anti-Leptin Polyclonal Antibody

A pairing test was performed by detecting a leptin standard sample (purchased from Abcam) as an antigen to be detected through the double antibody sandwich ELISA method using the labeled monoclonal antibodies secreted by the hybridoma cells prepared in Example 2 as a detection antibody and the polyclonal antibodies prepared in Example 3 as a capture antibody. A pair of antibodies with the highest detection signal was regarded as the most suitable pair of antibodies, which were retested and confirmed using human serum having a known leptin level.

The result showed that LEP-Ab-01 was the most suitable for pairing with LEP-Ab-02. LEP-Ab-01 recognizes leptin at the amino-terminus, and LEP-Ab-02 recognizes leptin at the carboxyl-terminus.

Example 5

Preparation of Leptin Detection Kit (1) Nanomagnetic bead coating: 50 mg of a suspension of carboxylated magnetic particles (with a particle size of 1 μm) was separated magnetically. The sediment retained, and then resuspended in 20 mM MES buffer (pH 5.5). 1 mL of 10 mg/mL EDC aqueous solution prepared freshly was added into the resuspended solution to activate the carboxyl groups on the surface of the magnetic beads, followed by 4 mg of LEP-Ab-02 prepared in Example 2. The resultant mixture was suspended at room temperature for 6 h and magnetically separated. The supernatant was discarded. The magnetic particles were resuspended in 100 mM Tris buffer (pH 8.0) containing 2% BSA to 1 mg/mL, to obtain coated magnetic particles, which were divided into 5 mL/bottle and stored at 4° C. for later use.

(2) Preparation of anti-leptin monoclonal antibody labeled with acridinium ester: To 50 μL of 25 mg/mL rabbit anti-leptin monoclonal antibody prepared in Example 3, 150 μL of 0.1 M carbonate buffer (pH 9.0) was added and mixed well. Then 1.5 μL of 5 mg/mL acridinium ester was added and mixed well. The resultant mixture was reacted in the dark at room temperature for 1.5 h and then taken out for desalting treatment in a 5 mL GE Desalting prepacked column. The chromatography column was first equilibrated using TBS. After adding the reacted acridinium ester solution, the protein samples at the peak were collected, divided into 5 mL/bottle and stored at 4° C. for later use.

(3) Preparation of leptin calibrator samples: leptin standard samples were formulated with buffer (40 mM Tris-Cl, 0.5% BSA, 1% NaCl, pH 8.0) as solutions at a concentration of 0 ng/mL, 20 ng/mL, and 60 ng/mL, respectively. They were lyophilized and stored at 0.5 mL/bottle at 4° C. for later use.

Example 6

Performance Evaluation for Leptin Detection Kit

The performance of the leptin detection kit prepared in Example 5 was evaluated by the double antibody sandwich method using a chemiluminescence analyzer as the detection tool. That is to say, the sample to be tested or the leptin standard sample was reacted with the anti-leptin polyclonal antibody (i.e. LEP-Ab-02)-coated magnetic particles for 10 min, followed by magnetic separation. Then the anti-leptin monoclonal antibody labeled with acridinium ester (i.e., acridinium ester-labeled LEP-Ab-01) was added and reacted for 10 min, followed by magnetic separation. Then the chemiluminescence pre-excitation solution and chemiluminescence excitation solution was added for luminescence reaction, and finally, the luminescence intensity was recorded to plot a standard curve ($R^2$ is greater than 0.99). According to the standard curve, the leptin content of the sample to be tested was calculated.

Sensitivity Testing:

Referring to the experimental protocol recommended by CLSI EP17-A, the sensitivity of the leptin detection kit prepared in Example 5 was calculated, giving the result of 0.5 ng/mL.

Linearity Testing:

A linear analysis was performed using the leptin detection kit of Example 5 and the standard samples each in a concentration of 0.5 ng/mL, 20 ng/mL, 40 ng/mL, 60 ng/mL, 80 ng/mL, and 100 ng/mL, respectively, to calculate a linear correlation coefficient (r), giving the r-value equaling to 0.9995. As calculated according to the experimental method recommended by CLSI EP17-A, the leptin detection kit of Example 5 is used to detect the deamidated gliadin antibody samples in a linear range from 0.5 ng/ml to 100 ng/mL.

Precision Testing:

Both the leptin samples at concentrations of 20 ng/mL and 60 ng/mL (prepared from standard leptin, purchased from Abcam) were tested in triplicate for each sample at each concentration and using three batches of kits of Example 5, to calculate intra-batch and inter-batch differences among the kits.

The calculation result showed that both the intra-batch and inter-batch differences for the leptin detection kit of Example 5 were less than 5%.

Interference Experiment

Both the leptin samples at concentrations of 20 ng/mL and 60 ng/mL were divided into six groups, into five of which various interfering substances were added respectively, and the remaining one was a control group. The added interfering substances were conjugated bilirubin, free bilirubin, hemoglobin, ascorbic acid, cholesterol and glycerides, and the ratio of the mass of the interfering substances to the mixed serum is 1:20. Then, the mixed serum with or without the various interfering substances was tested for leptin content to calculate the deviation there between. Deviation within ±10% was regarded as an acceptable range.

The results showed that for leptin detection kit of Example 5, the interference meets the criteria in the NCCLS document. This leptin detection kit of Example 5 can be used for an accurate assessment of the status of leptin in clinical laboratories.

Comparative Example 1

At present, the leptin content testing on the market adopts mostly enzyme-linked immunosorbent assay. In this experiment, Human leptin ELISA kit (10-23100, DSL, USA) is used for the comparative serum leptin testing.

Testing method: the performance evaluation was performed as same as that in Example 6 using the leptin calibrator samples, the quality control products, and the interfering experimental samples in Example 6. According to the instruction of the kit, the experiment was performed and the result were calculated. The result was evaluated by comparison with the leptin detection kits in Example 5 and Example 6.

The calculated result shows that the leptin determination kit has a coincidence rate of 90%, thus having a good consistency, with that of the Human leptin ELISA kit (10-23100, DSL, USA) in Comparative Example 1. Upon the performance evaluation, it shows that the leptin determination kit was superior to the comparative reagent in terms of sensitivity and anti-interference.

Comparative Example 2

A commercially available human leptin peptide segment (amino acid residues at positions 22 to 56, i.e., the specific amino acid sequence as set forth in SEQ ID NO. 3, namely VPIQKVQDDTKTLIKTIVTRINDISHTQSVSSKQK) was used as the immunogen for the preparation of a monoclonal antibody, designated C-Ab-10. In one embodiment, the method for preparing C-Ab-10 was substantially the same as the method for preparing LEP-Ab-01 in Example 2, except that the immunogen in Comparative Example 2 is the commercially available human leptin peptide segment (amino acid residues at positions 22 to 56).

Indirect ELISA was performed using a leptin standard sample (purchased from Abcam) as an antigen to be detected and labeled C-Ab-10 and labeled LEP-Ab-01 respectively as a detection antibody for titer comparison. results are as follows.

|  | Antibody | |
| --- | --- | --- |
| Antigen dilution fold | Lep-Ab-01 | C-Ab-10 |
|  | Antibody titer | |
| 10 | 3.367 | 2.090 |
| $10^2$ | 3.010 | 1.265 |
| $10^3$ | 1.863 | 0.724 |
| $10^4$ | 0.791 | 0.246 |
| $10^5$ | 0.254 | 0.052 |
| $10^6$ | 0.013 | 0.007 |
| PBS | 0.010 | 0.008 |

The results show that the monoclonal antibody prepared by using commercially available immunogen had a lower titer than LEP-Ab-01. The present monoclonal antibody prepared by the immunogen of the present application had better performance.

Comparative Example 3

A commercially available mouse leptin peptide segment (amino acid residues at positions 116 to 130, i.e., the specific amino acid sequence as set forth in SEQ ID NO. 4, namely SCSLPQTSGLQKPES) was used as the immunogen for preparation of a polyclonal antibody, designated LEPC-Ab-01. A pairing test was performed through the double antibody sandwich ELISA by using LEPC-Ab-01 and LEP-Ab-02 respectively as a capture antibody, LEP-Ab-01 as a detection antibody, and leptin standard sample and human serum with high-level leptin respectively as an antigen to be detected.

|  |  | Capture antibody | |
| --- | --- | --- | --- |
| Detection antibody | Antigen to be detected | LEP-Ab-02 | LEPC-Ab-01 |
|  |  | Titer | |
| LEP-Ab-01 | Leptin standard sample | 3.253 | 0.125 |
|  | Human serum | 3.124 | 0.089 |

The results show that the combination of LEPC-Ab-01 prepared by using the commercially available immunogen with LEP-Ab-01 had a lower titer than that of the combination of the present LEP-Ab-02 with LEP-Ab-01. The combination of polyclonal antibodies prepared by the present immunogen with LEP-Ab-01 had better performance.

The features of the above-mentioned embodiments can be combined arbitrarily. In order to make the description concise, all possible combinations of the various features in the foregoing embodiments are not described. However, the combination of these features should be considered within the scope of this specification, as long as they have no collision with each other.

The above-mentioned embodiments only present several embodiments of the present disclosure, whose descriptions are more specific and detailed but should not be thus understood as limiting the scope of the present disclosure. Therefore, the protection scope of the present disclosure should be subject to the appended claims.

What is claimed is:

1. A leptin immunogen, comprising a fragment of leptin, wherein the amino acid sequence of the fragment of leptin is as set forth in SEQ ID NO. 1, wherein the leptin immunogen does not comprise the full-length human leptin protein.

```
                              SEQUENCE LISTING

<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: human leptin peptide segment 1

<400> SEQUENCE: 1

Arg Ile Asn Asp Ile Ser His Thr Gln Ser Val Ser Ser Lys Gln Lys
1               5                   10                  15

Val Thr Gly Leu
            20

<210> SEQ ID NO 2
<211> LENGTH: 25
<212> TYPE: PRT
<213> ORGANISM: Artificial Sequence
<220> FEATURE:
<223> OTHER INFORMATION: human leptin peptide segment 2

<400> SEQUENCE: 2

Ser Cys His Leu Pro Trp Ala Ser Gly Leu Glu Thr Leu Asp Ser Leu
1               5                   10                  15

Gly Gly Val Leu Glu Ala Ser Gly Tyr
            20                  25

<210> SEQ ID NO 3
<211> LENGTH: 35
<212> TYPE: PRT
<213> ORGANISM: Artificial Sequence
<220> FEATURE:
<223> OTHER INFORMATION: commercially available human leptin peptide
      segment 1

<400> SEQUENCE: 3

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys
        35

<210> SEQ ID NO 4
<211> LENGTH: 15
<212> TYPE: PRT
<213> ORGANISM: Artificial Sequence
<220> FEATURE:
<223> OTHER INFORMATION: commercially available human leptin peptide
      segment 2

<400> SEQUENCE: 4

Ser Cys Ser Leu Pro Gln Thr Ser Gly Leu Gln Lys Pro Glu Ser
1               5                   10                  15
```

2. The leptin immunogen according to claim 1, wherein the leptin immunogen further comprises a carrier protein conjugated to the fragment of leptin.

3. A method for preparing hybridoma cells secreting an anti-leptin monoclonal antibody, comprising:
- immunizing an animal with an immunogen to obtain spleen cells from the immunized animal, wherein the immunogen is the leptin immunogen according to claim 1;
- fusing the spleen cells to myeloma cells and then screening to obtain positive fused cells; and
- subcloning the positive fused cells to obtain the hybridoma cells secreting the anti-leptin monoclonal antibody.

4. Hybridoma cells secreting an anti-leptin monoclonal antibody, prepared by the method for preparing hybridoma cells secreting an anti-leptin monoclonal antibody according to claim 3.

5. The method according to claim 3, wherein the leptin immunogen further comprises a carrier protein conjugated to the fragment of leptin.

6. The leptin immunogen according to claim 2, wherein the carrier protein is selected from hemocyanin, bovine serum albumin, chicken ovalbumin, rabbit serum albumin, and fibrinogen.

7. The method according to claim 5, wherein the carrier protein is selected from hemocyanin, bovine serum albumin, chicken ovalbumin, rabbit serum albumin, and fibrinogen.

* * * * *